US011278502B2

(12) United States Patent
Kulkarni et al.

(10) Patent No.: US 11,278,502 B2
(45) Date of Patent: Mar. 22, 2022

(54) MODIFIED RELEASE FORMULATION OF LACOSAMIDE

(71) Applicant: LUPIN LIMITED, Maharashtra (IN)

(72) Inventors: Shirishkumar Kulkarni, Maharashtra (IN); Satish Kumar Dalal, Maharashtra (IN); Harshal Jahagirdar, Maharashtra (IN); Kishore Kumar Konda, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 16/146,237

(22) Filed: Sep. 28, 2018

(65) Prior Publication Data

US 2019/0029968 A1 Jan. 31, 2019

Related U.S. Application Data

(63) Continuation of application No. 13/505,990, filed as application No. PCT/IN2010/000722 on Nov. 3, 2010, now Pat. No. 10,786,464.

(30) Foreign Application Priority Data

Nov. 3, 2009 (IN) .......................... 1309/KOL/2009
Mar. 16, 2010 (IN) ............................ 258/KOL/2010

(51) Int. Cl.
*A61K 9/50* (2006.01)
*A61K 47/38* (2006.01)
*A61K 31/165* (2006.01)
*A61K 9/20* (2006.01)
*A61K 47/32* (2006.01)

(52) U.S. Cl.
CPC .......... *A61K 9/5078* (2013.01); *A61K 9/2077* (2013.01); *A61K 31/165* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,369,172 A | 1/1983 | Schor et al. | |
| 5,654,301 A | 8/1997 | Kohn et al. | |
| 5,773,475 A | 6/1998 | Kohn | |
| 6,627,223 B2 | 9/2003 | Percel et al. | |
| RE38,551 E | 7/2004 | Kohn | |
| 2004/0214893 A1* | 10/2004 | Peterson | C07C 57/145 514/561 |
| 2005/0277579 A1* | 12/2005 | Krishnan | A61K 31/155 514/369 |
| 2006/0100157 A1* | 5/2006 | Rauschkolb-Loffler | A61K 31/165 514/7.3 |
| 2006/0135437 A1* | 6/2006 | Stoehr | A61K 31/16 562/553 |
| 2006/0165745 A1 | 7/2006 | Chew et al. | |
| 2007/0042969 A1 | 2/2007 | Rauschkolb-Loffler et al. | |
| 2007/0043120 A1 | 2/2007 | Beyreuther et al. | |
| 2007/0071819 A1* | 3/2007 | Kesarwani | A61K 9/1652 424/468 |
| 2009/0298947 A1* | 12/2009 | Mundorfer | A61K 31/165 514/616 |
| 2010/0120906 A1 | 5/2010 | Nadjsombati | |

FOREIGN PATENT DOCUMENTS

| | | |
|---|---|---|
| DE | 10 2008 059 155 A1 | 6/2010 |
| JP | 2006-124385 A | 5/2006 |
| WO | 2006/036007 A2 | 4/2006 |
| WO | WO 2007/120485 * | 10/2007 |
| WO | WO 2008/086492 A1 | 7/2008 |
| WO | WO 2009/146325 A1 | 12/2009 |
| WO | WO 2010/009433 A1 | 1/2010 |
| WO | WO 2010/018408 A2 | 2/2010 |
| WO | 2010/060624 A2 | 6/2010 |

OTHER PUBLICATIONS

Beyreuther et al. (CNS Drug Reviews, 13(1), 21-42, 2007) Lacosamide: A Review of Preclinical Properties.*
Errington et al. "The investigational Anticonvulsant Lacosamide Selectively Enhances Slow Inactivation of Voltage-Gated Sodium Channels", Molecular Pharmacology, 73(1), 157-169 (2008).
International Search Report for International Application No. PCT/IN2010/000722, dated Apr. 21, 2011.
"Assessment Report for Vimpat," European Medicines Agency, 2008.
Vimpat film coated tablet (European Medicine Agency, 2008) Summary of Product Charcterstics.
Jantzen, G. M., and Robinson, J. R. "Sustained-and Controlled-Release Drug Delivery Systems," Modern Pharmaceutics, Marcel Dekker, Inc.,Third Edition, (1996), pp. 575-580.
Vimpat® (Lacosamide), FDA Approved Labeling Text—NDA 22-253 and 22-254, dated Oct. 28, 2008, pp. 1-29.
Beyreuther et al., "Lacosamide: A Review of Preclinical Properties," CNS Drug Review (2007), 13(1):21-42.
Li et al., "The Use of Hypromellose in oral drug delivery," Journal of Pharmacy and Pharmacology (2005), 57:533-546.
Craig, Paul. N., "Synthesis of Ion Exchange Resins," Annals of the New York Academy of Sciences (1959), 67-78.
Renade et al., "Drug Delivery Systems (Second Edition)," CRC Press Pharmacology & Toxicology Series (2004), p. 167.
Ion-exchange resin—Encyclopedia Britannica (https://www.britannica.com/science/ion-exchange-resin, printed Jul. 7, 2020).
Ion-exchange resin—Wikipedia (https://en.wikipedia.org/wiki/Ion-exchange_resin, printed Jul. 7, 2020).
Jul. 16, 2020 Notice of Opposition to a European Patent issued by the European Patent Office for European Patent No. EP 2 496 220.

(Continued)

*Primary Examiner* — Tigabu Kassa
(74) *Attorney, Agent, or Firm* — Duane Morris LLP

(57) ABSTRACT

The present invention provides a modified release formulation of lacosamide. The modified release formulation of the present invention comprising lacosamide and modified release polymer provides modified release of lacosamide with minimal $C_{max}$ to $C_{min}$ peak to trough variation over a period of at least 12 hrs.

24 Claims, 2 Drawing Sheets

(56) References Cited

OTHER PUBLICATIONS

Jul. 16, 2020 Consolidated List of References for Opposition for European Patent No. EP 2 496 220.
Nov. 26, 2020 Reply to European Patent Opposition for European Patent No. EP 2 496 220.
Mar. 31, 2021 Summons to Attend Oral Proceedings Pursuant to Rule 115(1) EPC for European Patent No. EP 2 496 220.

\* cited by examiner

MODIFIED RELEASE FORMULATION OF LACOSAMIDE

This application is a Continuation Application of U.S. patent application Ser. No. 13/505,990, filed 3 May 2012, which is a National Stage Application of PCT/IN2010/000722, filed 3 Nov. 2010, which claims benefit of Serial No. 258/KOL/2010, filed 16 Mar. 2010 in India, and which also claims benefit of Serial No. 1309/KOL/2009, filed 3 Nov. 2009 in India and which applications are incorporated herein by reference. To the extent appropriate, a claim of priority is made to each of the above disclosed applications.

FIELD OF THE INVENTION

The present invention relates to a modified release formulation of antiepileptic drug. The formulation of the present invention comprises lacosamide or pharmaceutically acceptable salts, esters, metabolites, prodrugs or enantiomers thereof and modified release polymer.

BACKGROUND OF THE INVENTION

The term epilepsy is derived from a Greek word meaning a condition of being seized or overcome. The term epilepsy designates a group of central nervous system disorders having in common the occurrence of sudden and transitory episodes of abnormal behavioral symptoms of motor sensory, autonomic or psychic origin. Epilepsies have a definite onset and ending, and they usually are of short duration.

Epileptic seizures are mainly of two types: partial seizures and generalized seizures. Partial seizures can again be of three type; i.e. simple partial, complex partial and partial with secondarily generalized tonic clonic seizure. Generalized seizures are classified as absence seizure, myoclonic seizure and tonic-clonic seizure. Anti-epileptic drug are vital in preventing fits for people with epilepsy, thereby greatly enhancing quality of life.

Based on their mechanism of action, anti-epileptic drugs can be classified as sodium channel blockers, calcium current inhibitors, gamma-aminobutyric acid (GABA) enhancers, glutamate blockers, carbonic anhydrase inhibitors etc.

Drugs such as acetazolamide, carbamazepine, clobazam, clonazepam, ethosuximide, gabapentin, lamotrigine, levetiracetam, oxcarbazepine, phenobarbital (phenobarbitone), phenytoin, pregabalin, primidone, rufinamide, sodium valproate, tiagabine, topiramate, valproic acid, vigabatrin, zonisamide, valpromide, divalproex sodium, gabapentin, felbamate, fosphenytoin and the like are used for the treatment of epilepsy.

Anti-epileptic drugs (AEDs) are also promising agents for the prevention of migraine and other head pain. Migraine and epilepsy share several clinical features and respond to many of the same pharmacological agents, suggesting that similar mechanisms may be involved in their pathophysiology.

The most common side effects associated with epilepsy medicines are drowsiness, irritability, nausea, rash, and clumsiness. Some drugs produce changes in emotions, memory or behavior, or affect learning. Modified release formulations of anti-epileptic drugs provides reduction in the above mentioned side effects, increased patient compliance, avoids a typical peak-valley plasma concentration profile and ultimately reduction in the precipitation of adverse effects especially of a drug with a narrow therapeutic index whenever overmedication occurs.

Lacosamide, marketed as Vimpat®, is approved in US for the treatment of partial-onset seizure in patient with epilepsy aged 17 years and older. The lacosamide may be used for the treatment or prophylaxis of migraine, fibromyalgia syndrome, osteoarthritis, post herpetic neuralgia and painful diabetic neuropathy. Chemically lacosamide is (2R)-2-(acetylamino)-3-methoxy-N-(phenylmethyl)propanamide, R-enantiomer is at least 10-fold more active than the S-enantiomer. U.S. Pat. No. 5,654,301 discloses aminoacid derivative, lacosamide exhibiting anticonvulsant properties. RE 38,551 discloses the novel enantiomeric compounds one of which is lacosamide.

Vimpat® is approved for oral or intravenous administration. Lacosamide for oral use has the initial dose of 50 mg twice daily (100 mg per day). It can be increased at weekly intervals by 100 mg/day (two divided doses) up to the recommended maintenance dose of 200 to 400 mg/day, based on individual patient response and tolerability. The marketed formulation Vimpat® is an immediate release formulation for BID administration The side effect associated with lacosamide is similar to other epileptics as dizziness, ataxia, vomiting, diplopia, nausea, vertigo and vision blurred.

There exists a need for modified release formulation of lacosamide which controls the release of lacosamide in such a manner that therapeutically effective concentration is maintained in the blood for an extended period of time keeping the drug concentration in the blood substantially constant. The use of modified release formulations of lacosamide would improve patient compliance as it reduces the numbers of dosages to be taken per day.

With the modified release formulation, the therapy may be continued without interrupting the sleep of the patient, which is of special importance when treating an epileptic patient to prevent nocturnal seizures, or patients with pain who experience severe pain on awakening, as well as for debilitated patients for whom an uninterrupted sleep is essential.

Thus the modified release formulation of lacosamide would provide a modified release of lacosamide with minimal $C_{max}$ to $C_{min}$ peak to trough variation over a period of at least 12 hrs. It is preferred that the modified release formulation of lacosamide is capable of maintaining a substantially constant plasma level of lacosamide for at least 12 hrs.

SUMMARY OF THE INVENTION

In one embodiment, the modified release formulation of lacosamide comprises lacosamide and modified release polymer.

In other embodiment, the modified release formulation of lacosamide further comprises core comprising lacosamide and modified release coating.

In another embodiment, the modified release formulation further comprises:
  (i) a core comprising non-pareil seed;
  (ii) coating the non-pareil seed with lacosamide; and
  (iii) modified release coating.

In further embodiment, the modified release formulation of lacosamide releases not more than about 25% of lacosamide within 1 hour, from about 30% to about 70% of lacosamide within 4 hour and not less than 75% of lacosamide within 12 hours when tested according to USP type 1 dissolution apparatus at 100 rpm and 37° C. temperature in 900 ml of 0.1N HCl.

In further embodiment, the modified release formulation comprising lacosamide and modified release polymer, said modified release formulation administered as a single dose provides an invivo plasma profile selected from:
(i) Mean $T_{max}$ of about 5 or more hours, or
(ii) Mean $C_{max}$ of less than about 4600 ng/ml, or
(iii) Mean $AUC_{0-72}$ of more than about 78500 ng·hr/ml

DETAILED DESCRIPTION OF THE INVENTION

Figure 1:
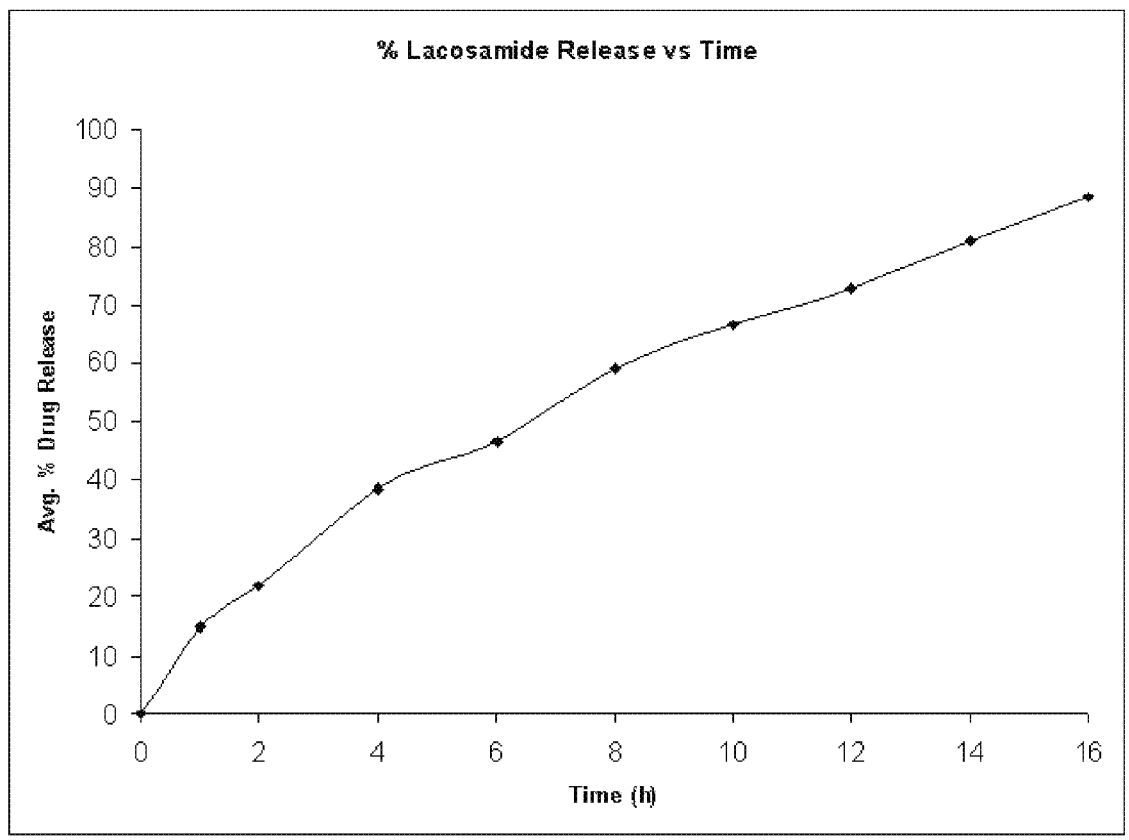
FIG. 01 is a graph depicts the dissolution profile in 0.1N HCl of the formulations as described in Example 03.

The invention provides a modified release formulation of antiepileptic drug preferably lacosamide and modified release polymer.

The antiepileptic drug includes sodium channel blockers, calcium current inhibitors, gamma-aminobutyric acid (GABA) enhancers, glutamate blockers, carbonic anhydrase inhibitors and any other drug which has similar action.

The antiepileptic drug can be selected from the group consisting of lacosamide; acetazolamide; carbamazepine; clobazam; clonazepam; ethosuximide; gabapentin; lamotrigine; levetiracetam; oxcarbazepine; phenobarbital (phenobarbitone); phenytoin; pregabalin; primidone; rufinamide; sodium valproate; tiagabine; topiramate; valproic acid; vigabatrin; zonisamide; valpromide; divalproex sodium; gabapentin; felbamate; fosphenytoin; and combination thereof. Other drugs which have anti epileptic or antimigraine activity are also within the scope of the invention. The preferred antiepileptic drug is lacosamide.

As used herein the term "lacosamide" refers to N2-acetyl-N-benzyl-D-homoserinamide including its R and S enantiomers and racemic mixtures or pharmaceutically acceptable salts, esters, prodrugs or metabolites. The R enantiomer of N2-acetyl-N-benzyl-D-homoserinamide is the preferred enantiomer and the marketed immediate release preparation Vimpat® contains the R enantiomer. The modified release formulation preferably contains between 10-1000 mg of lacosamide. It has been known that pharmacokinetics of lacosamide is dose proportional at the therapeutic range.

The term "formulation" or "composition" as used herein refers to the drug in combination with pharmaceutically acceptable excipients. This includes orally administrable formulations as well as formulations administrable by other means.

"Modified release formulation" as used herein means a pharmaceutical formulation which releases the drug substance at a slower rate than from an immediate release formulation.

The term modified release formulation can be used interchangeably with prolonged release formulation, programmed release formulation, timed release formulation, extended release formulation, site specific release formulation, sustained release formulation, controlled release formulation, slow release formulation, delayed release formulation, osmotic dosage form, bioadhesive formulation, orally disintegrating modified release formulation and other such dosage forms.

The modified release formulation is preferably administered once a day (QD).

"Pharmaceutically acceptable" is meant a carrier comprised of a material that is not biologically or otherwise undesirable.

The term "therapeutic effective concentration" is used throughout the specification to describe concentration of lacosamide which is therapeutically effective in treatment and prophylaxis of diseases where lacosamide is effective.

The term "relative bioavailability" herein denotes AUC for a specific orally administered composition expressed as a percentage of AUC for an orally administered dosage form of the active ingredient at the same dosage rate.

The terms "$AUC_{0-72}$" herein mean the area under the curve relating blood plasma concentration to time after administration from 0 to 72 hours, as determined using the linear trapezoidal rule, and are expressed in units of (ng·h/ml).

The term "$AUC_{0-\infty}$" herein means the area under the curve relating blood plasma concentration to time from time 0 hours to infinity, and is expressed in units of (ng·h/ml).

The term "$AUC_{0-\tau}$" herein means area under the blood plasma concentration to time curve from time zero to time tau over a dosing interval at steady state, where tau is the length of the dosing interval, and is expressed in units of (ng·h/ml).

The term "$C_{max}$" herein means the maximum observed blood plasma concentration or the maximum blood plasma concentration calculated or estimated from a concentration to time curve, and is expressed in units of ng/ml.

The term "$C_{min}$" herein means the minimum observed blood plasma concentration or the maximum blood plasma concentration calculated or estimated from a concentration to time curve, and is expressed in units of ng/ml.

The term "$C_{avg}$" as used herein, means the plasma concentration of the drug within the dosing interval, and is calculated as AUC/dosing interval, and is expressed in units of ng/ml.

The term "$T_{max}$" herein means the time after administration at which $C_{max}$ occurs, and is expressed in units of hours (h).

The term "single dose" means that the human patient has received a single dose of the drug formulation and the drug plasma concentration has not achieved steady state.

The term "steady state" means that the blood plasma concentration curve for a given drug does not substantially fluctuate after repeated doses to dose of the formulation.

The term "Degree of Fluctuation" is expressed as $(C_{max}-C_{min})/C_{avg}$.

The term "bioequivalence" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study.

The modified release formulation includes tablets, coated tablets, layered tablets, granules, powders, microparticles, capsules which may be hard gelatin or soft gelatin, caplets, sachets, pellets, spheroids, mini-tablets, beads, microcapsules and pills.

One embodiment discloses the modified release dosage form of lacosamide comprising lacosamide and modified release polymer.

Other embodiment discloses the modified release formulation of lacosamide and modified release polymer which provides therapeutically effective concentration of lacosamide for a period of at least 8 hrs preferably 24 hrs or more.

Another embodiment discloses the modified release formulation which releases the active ingredient lacosamide—over a period of at least 4 hrs, preferably at least 8 hrs and more preferably of at least 12 hrs.

In further embodiment, the modified release formulation comprising lacosamide and modified release polymer, said modified release formulation administered as a single-dose provides an invivo plasma profile selected from:
(i) Mean $T_{max}$ of about 5 or more hours, or
(ii) Mean $C_{max}$ of less than about 4600 ng/ml, or
(iii) Mean $AUC_{0-72}$ of more than about 78500 ng·hr/ml
Lacosamide is administered as a single dose in the dose range of 50 to 800 mg, preferably 100 to 600 mg and more preferably in the dose of 200 mg.

Further it is contemplated that at given plasma level of lacosamide per specified dose will be directly proportional to other doses of lacosamide. Such proportional dose and plasma levels are contemplated to be within the scope of the claimed invention.

The modified release polymer may be selected from hydrophilic polymer, hydrophobic polymer or wax. The hydrophilic polymer may be selected from the group consisting of cellulose derivatives such as methyl cellulose, hydroxypropyl methylcellulose (hypromellose), hydroxyethyl cellulose, hydroxypropyl cellulose, hydroxyethyl methylcellulose, carboxymethylcellulose and sodium carboxymethylcellulose; vinyl pyrrolidone polymers such as polyvinylpyrrolidone and copolymers of vinyl pyrrolidone and vinyl acetate; alkylene oxide such as polyethylene oxide; polysaccharides such as chitosan; gellan; xanthan gum; gums of plant, animal, mineral or synthetic origin; and alginic acid derivatives such as alginic acid and its physiologically acceptable salts such as sodium, potassium or calcium.

Hydrophobic polymer may be selected from the group consisting of ethyl cellulose; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); poly (vinyl acetate); poly vinyl alcohols; and polyacrylamide derivatives.

Wax may be selected from the group consisting of glycerol palmitostearate; beeswax; glycowax; castor wax; carnauba wax; glycerol monostearate; stearyl alcohol; glycerol behenic acid ester; cetyl alcohol; natural and synthetic glycerides; waxes; fatty acids; and hydrogenated vegetable oil.

In one embodiment the modified release polymer used in the modified release formulation may be bioadhesive.

The bioadhesive polymers may be selected from the group consisting of proteins (e.g., hydrophilic proteins) such as pectin, zein, modified zein, casein, gelatin, gluten, plasma albumin and collagen; chitosan; oligosaccharides; polysaccharides such as cellulose, dextrans, tamarind seed polysaccharide, gellan, carrageenan, xanthan gum, gum arabic, hyaluronic acid, polyhyaluronic acid, alginic acid and sodium alginate; polyamides; polycarbonates; polyalkylenes; polyalkylene glycols; polyalkylene oxides; polyalkylene terephthalates; polyvinyl alcohols; polyvinyl ethers; polyvinyl esters; polyvinyl halides; polyvinylpyrrolidone; polyglycolides; polysiloxanes; polyurethanes; polystyrene; polymers of acrylic and methacrylic esters; polylactides; poly(butyric acid); poly(valeric acid); poly(lactide-co-glycolide); polyanhydrides; polyorthoesters; poly(fumaric acid); poly(maleic acid); and blends or copolymers or mixtures thereof.

Combination of modified release polymers is also included within the scope of the invention.

The amount of modified release polymers may range from about 10-90%.

The modified release formulation may further contain pharmaceutically acceptable excipients such as binders; diluents; lubricants; disintegrating agents; glidants; stabilizers; and surface active agents.

The binders may be selected from potato starch; modified starch; gelatin; wheat starch; corn starch; microcrystalline cellulose; celluloses such as hydroxypropyl cellulose, hydroxyethyl cellulose, hydroxypropylmethyl cellulose (Hypromellose), ethyl cellulose and sodium carboxy methyl cellulose; natural gums such as acacia, alginic acid and guar gum; liquid glucose; dextrin; povidone; syrup; polyethylene oxide; polyvinyl pyrrolidone; poly vinyl alcohol; poly-N-vinyl amide; polyethylene glycol; gelatin; poly propylene glycol; tragacanth; hydrogenated vegetable oil; castor oil; paraffin; higher aliphatic alcohols; higher alphatic acids; long chain fatty acids; fatty acid esters; and wax-like materials such as fatty alcohols, fatty acid esters, fatty acid glycerides, hydrogenated fats, hydrocarbons, nor-50 mal waxes, stearic acid and stearyl alcohol. The amount of binder present can vary from about 0.1% to about 25% by weight of the tablet dry weight, preferably about 0.5% to about 10%.

The diluent may be selected from pharmaceutically acceptable inert fillers such as microcrystalline cellulose; lactose; dibasic or tribasic calcium phosphate; saccharides confectioner's sugar; compressible sugar; dextrates; dextrin; dextrose; fructose; lactitol; mannitol; sucrose; starch xylitol; sorbitol; talc; calcium carbonate; or calcium sulphate. The diluent is preferably used in an amount of about 10 to 90% by weight.

The disintegrating agent may be selected from cross-linked polymers such as crospovidone; starch or modified starch such as sodium starch glycolate; clays such as bentonite or veegum; celluloses or cellulose derivatives or crosslinked cellulose such as croscarmellose sodium; or resins such as polacrillin potassium.

The lubricant may be selected from Mg, Al or Ca or Zn stearate; polyethylene glycol; glyceryl behenate; glyceryl monosterate; mineral oil; sodium stearyl fumarate; stearic acid; hydrogenated vegetable oil; talc; hydrogenated soybean oil; stearyl alcohol; leucine; polyethylene glycol; ethylene oxide polymers; or colloidal silica.

The glidant may be selected from magnesium trisilicate; powdered cellulose; starch; talc and tribasic calcium phosphate; calcium silicate; magnesium silicate; colloidal silicon dioxide; or silicon hydrogel.

The modified release formulation may optionally contain a surface active agent. The preferred surface active agent may be selected from a group consisting of fatty acid; olefin; alkylcarbonyl; silicon elastomer; sulfate ester; petty alcohol sulfate; sulfate pete and oil; sulfonic acid-base; fat sulfonate; alkylaryl sulfonate; ligmin sulfonate; phosphoric acid ester; polyoxyethylene; polyoxyethylene caster oil; polyglycerol; polyol; imidazol; altanolamine; hetamine; sulfobecamine; phosphotide; polyoxyethylene-sorbitan fat acid ester (Tween); and sorbitan ester (Span).

The osmotic agents may be selected from sodium chloride; potassium chloride; magnesium sulfate; magnesium chloride; sodium sulfate; lithium sulfate; urea; inositol; sucrose; lactose; glucose; sorbitol; fructose; mannitol; dextrose; magnesium succinate or potassium acid phosphate.

In one of the embodiment the modified release formulation comprises lacosamide and modified release polymer which may optionally coated.

The coating may be modified release coating which may modify the release of drug from modified release formulation or coating which does not alter the release of drug from the modified release formulation.

Commercially available, ready-to-coat preparations, sold under various brand names such as various grades of Opadry®. Opadry® is a film coating system comprising hypromellose, polyethylene glycol and titanium dioxide which does not alter the release of drug from modified release formulation may also be used.

Examples of modified release coating include functional coating; moisture barrier coatings; enteric polymeric coatings; sustained release coating; and the like.

In one embodiment the modified release formulation further comprises core comprising lacosamide and modified release coating.

In other embodiment the modified release formulation comprises a core comprising lacosamide and modified release coating which provides therapeutically effective concentration of lacosamide for a period of at least 8 hrs preferably 24 hrs or more.

The core may further comprise pharmaceutically acceptable excipients.

In another embodiment, the modified release formulation further comprises:
(i) a core comprising non-pareil seed;
(ii) coating the non-pareil seed with lacosamide; and
(iii) modified release coating In another embodiment, the modified release formulation further comprises:
(i) a core comprising non-pareil seed;
(ii) coating the non-pareil seed with lacosamide; and
(iii) modified release coating which provides therapeutically effective concentration of lacosamide for a period of at least 8 hrs preferably 24 hrs or more.

The non-pareil seed may be selected from sugar spheres, microcrystalline cellulose or other inert material.

The modified release coating comprises of modified release polymer and other pharmaceutically acceptable excipients. The modified release polymer includes hydrophilic polymer, hydrophobic polymer or wax as disclosed above.

The modified release coating composition may comprise of cellulosic polymer selected form hydroxypropyl cellulose (HPC); hydroxyethyl cellulose; hydroxypropyl methylcellulose (hypromellose); methyl cellulose; ethyl cellulose; cellulose acetate; cellulose acetate butyrate; cellulose acetate phthalate; cellulose acetate succinate; cellulose acetate propionate; cellulose acetate trimellitate; hydroxypropylmethyl cellulose phthalate; hydroxypropylmethyl cellulose succinate; hydroxypropylmethyl cellulose acetate succinate; cellulose acetate succinate butyrate; cellulose acetate succinate propionate; carboxymethylcellulose sodium, cellulose butyrate; and mixtures thereof; pH-independent acrylates such as Eudragit RS, Eudragit RL and the like; pH-dependent polymers such as poly(methacrylic acid, methylmethacrylate) 1:1, poly(methacrylic acid, ethylacrylate) 1:1, poly(methacrylic acid, methylmethacrylate) 1:2, and the like or waxes such as polyethylene glycol.

The modified release coating may be aqueous, nonaqueous or combination of the two.

If desired, the permeability of the modified release coating may be adjusted by blending of two or more excipients.

The porosity of the modified release coating may be modified by using pore forming agents. The pore forming agents may be selected from crystals of sucrose; mannitol; sorbitol; or salts such as sodium chloride or potassium chloride.

The modified release coating composition may further include other pharmaceutically acceptable excipients such as plasticizer, solvent system (i.e., water), a colorant to provide elegance and product distinction. Color may be added to the solution of the therapeutically active agent instead, or in addition to the overcoat. Suitable ingredients for providing color to the formulation include titanium dioxide and color pigments, such as iron oxide pigments. The incorporation of pigments, may, however, increase the retard effect of the coating. Alternatively, any suitable method of providing color to the formulations of the present invention may be used.

The plasticizer may be selected from the group consisting of one or more of polyethylene glycol; triethyl citrate; triacetin; diethyl phthalate; dibutyl stearate; dibutyl sebacate; oleic acid; alcohol; mineral oil; castor oil; lanolin; petrolatum; propylene glycol; and glycerol.

The modified release formulation may be manufactured by various methods known in the art such as by dry granulation, wet granulation, melt granulation, direct compression, double compression, extrusion spheronization, layering and the like. Compaction of the blend into coprimate may be carried out using a slugging technique or roller compaction. The milling of the granules may be carried out according to conventional milling methods.

The process of wet granulation includes aqueous or non-aqueous solvents.

The coating operation may be conducted in standard equipment such as a fluid bed coater, a wurster coater or a rotary bed coater.

The invention is not to be limited in scope by the specific embodiments described herein. Indeed, various modifications of the invention in addition to those described herein will become apparent to those skilled in the art from the foregoing description. Such modifications are intended to fall within the scope of the appended claims.

Example 01

| Sr. No. | Ingredients | % w/w |
| --- | --- | --- |
| 1 | Lacosamide | 32.26 |
| 2 | Polyethylene Oxide | 24.19 |
| 3 | Hypromellose | 8.06 |
| 4 | Mannitol | 32.27 |
| 5 | Colloidal silicon dioxide | 1.61 |
| 6 | Magnesium Stearate | 1.61 |

Film Coating: 2-3%

Procedure:
1. Sift all ingredients through suitable sieve
2. Blend and mix together Lacosamide, Polyethylene Oxide and Hypromellose in a suitable blender.
3. Add Mannitol to Step 2 and mix till uniform blend is obtained.
4. Mix Step 3 with Colloidal silicon dioxide and lubricate with Magnesium Stearate for 5 minutes.
5. Compress the step 4 into tablet using suitable punch tooling.
6. Coat the tablets with coating solution either organic or aqueous or semiaqueous solution.

Example 02

| Sr. No. | Ingredients | % w/w |
| --- | --- | --- |
| 1 | Lacosamide | 32.26 |
| 2 | Microcrystalline cellulose | 28.23 |
| 3 | Polyvinylpyrrolidone | 4.03 |
| 4 | Polyethylene Oxide | 24.19 |
| 5 | Hypromellose | 8.06 |
| 6 | Solvent | Q.S. |
| 7 | Colloidal silicon dioxide | 1.61 |
| 8 | Magnesium Stearate | 1.61 |

Film Coating: 2-3%

Procedure:
1. Sift all ingredients through suitable sieve.
2. Blend and mix together Lacosamide and Microcrystalline cellulose in a suitable blender and load in RMG.
3. Dissolve and prepare a clear solution of Polyvinylpyrrolidone in solvent.
4. Granulate the Step 2 with the solution from step 3 and dry the granules in Dryer and mill/size them by passing through suitable mesh.
5. Mix and blend the step 4 with Polyethylene Oxide, Hypromellose to form a uniform blend.
6. Mix Step 5 with Colloidal silicon dioxide and lubricate with Magnesium Stearate for 5 minutes.
7. Compress the step 6 into tablet using suitable punch tooling.
8. Coat the tablets with coating solution either organic or aqueous or semiaqueous solution.

Example 03

| Sr. No. | Ingredients | % w/w |
| --- | --- | --- |
| 1 | Lacosamide | 19.05 |
| 2 | Hypromellose | 28.57 |
| 3 | Microcrystalline cellulose | 23.81 |
| 4 | Copovidone | 23.81 |
| 5 | Aerosil | 2.86 |
| 6 | Magnesium Stearate | 1.90 |
| 7 | Solvent | Q.S. |

Procedure:
1. Sift Lacosamide, Hypromellose and Microcrystalline cellulose through 30# sieve.
2. Dissolve Copovidone in solvent.
3. Granulate step 1 with the solution of step 2.
4. Dry the granules at 45° C. and then pass through 20# sieve.
5. Sift Microcrystalline cellulose, Crospovidone and Aerosil through 40# sieve.
6. Lubricate step 5 by using Mg-stearate passed through 60# sieve.
7. Compress step 6 by using suitable punch.
8. Coat the tablet of Step 7 by using Opadry coating solution (2-3% wt. Gain)

Example 04

| Sr. No. | Ingredients | % w/w |
| --- | --- | --- |
| 1 | Lacosamide | 33.33 |
| 2 | Hydrogenated Vegetable Oil | 8.33 |
| 3 | Microcrystalline cellulose | 34.17 |
| 4 | Stearic acid | 4.17 |
| 5 | Polyethylene glycol | 16.67 |
| 6 | Solvent | Q.S. |
| 7 | Colloidal silicon dioxide | 1.67 |
| 8 | Magnesium Stearate | 1.67 |

Film Coating: 2-3%

Procedure:
1. Sift all ingredients through suitable sieve.
2. Add and melt Hydrogenated Vegetable Oil, Polyethylene glycol and Stearic acid in preheated steam jacketed vessel at 60-70° C. and to this melted mass, add Lacosamide and stearic acid under stirring, stop the heating and continue the stirring for 30-45 min until a uniform mass is formed.
3. Cool the molten uniform mass to room temperature and mill the solidify mass in co-mill using suitable sieve.
4. Mix and blend the step 3 with Microcrystalline cellulose for 5-10 minutes.
5. Mix Step 4 with Colloidal silicon dioxide and lubricate with Magnesium Stearate for 5 minutes.
6. Compress the step 5 into tablet using suitable punch tooling.
7. Coat the tablets with coating solution either organic or aqueous or semiaqueous solution.

Example 05

| Sr. No. | Ingredients | % w/w |
| --- | --- | --- |
| | Ist Layer | |
| 1 | Lacosamide | 20.00 |
| 2 | Hypromellose | 21.50 |
| 3 | Microcrystalline cellulose | 11.50 |
| 4 | Copovidone | 15.00 |
| 5 | Aerosil | 1.00 |
| 6 | Magnesium Stearate | 1.00 |
| 7 | Solvent | Q.S. |
| | IInd Layer | |
| 1 | Polyethylene oxide | 170.59 |
| 2 | Sodium Chloride | 76.47 |
| 3 | Hypromellose | 35.88 |
| 4 | Hydroxypropyl cellulose | 9.41 |
| 5 | Red iron oxide | 0.59 |
| 6 | Magnesium Stearate | 7.06 |
| 7 | Solvent | Q.S. |

Procedure:
First Layer
1. Sift Lacosamide, Hypromellose and Microcrystalline cellulose through 30# sieve.
2. Dissolve Copovidone in solvent.
3. Granulate step 1 with the solution of step 2.
4. Dry the granules at 45° C. and then passed through 20# sieve.
5. Sift Crospovidone and Aerosil 200 through 40# sieve.
6. Lubricate step 5 by using Magnesium Stearate passed through 60# sieve.
Second Layer
1. Sift Polyethylene oxide, Sodium Chloride, Hypromellose, Hydroxypropyl cellulose and Red iron oxide through 40# sieve.

2. Granulate step 1 by using solvent.
3. Dry the granules at 45° C. and then passed through 20# sieve.
4. Lubricate step 3 by using Magnesium Stearate passed through 60# sieve.

Compression

Compress both layers by using suitable punch

Coating:

Coat the compressed tablet by using Opadry coating solution (2-3% wt. Gain)

Example 06

| Sr. No. | Ingredients | % w/w |
|---|---|---|
| 1 | Lacosamide | 32.26 |
| 2 | Microcrystalline cellulose | 28.23 |
| 3 | Polyvinylpyrrolidone | 4.03 |
| 4 | Xanthum Gum | 24.19 |
| 5 | Hypromellose | 8.06 |
| 6 | Solvent | Q.S. |
| 7 | Colloidal silicon dioxide | 1.61 |
| 8 | Magnesium Stearate | 1.61 |

Film Coating: 2-3%

Procedure:
1. Sift all ingredients through suitable sieve
2. Blend and mix together Lacosamide and Microcrystalline cellulose in a suitable blender and load in Rapid Mixer Granulator.
3. Dissolve and prepare a clear solution of Polyvinylpyrrolidone in solvent.
4. Granulate the Step 2 with the solution from step 3 and dry the granules in Dryer and mill/size them by passing through suitable mesh.
5. Mix and blend the step 4 with Xanthum Gum, Hypromellose to form a uniform blend.
6. Mix Step 5 with Colloidal silicon dioxide and lubricate with Magnesium Stearate for 5 minutes.
7. Compress the step 6 into tablet using suitable punch tooling.
8. Coat the tablets with coating solution either organic or aqueous or semiaqueous solution

Example 07

| Sr. No. | Ingredients | % w/w |
|---|---|---|
| 1 | Lacosamide | 32.26 |
| 2 | Microcrystalline cellulose | 28.23 |
| 3 | Polyvinylpyrrolidone | 4.03 |
| 4 | Sodium alginate | 24.19 |
| 5 | Hypromellose | 8.06 |
| 6 | Solvent | Q.S. |
| 7 | Colloidal silicon dioxide | 1.61 |
| 8 | Magnesium Stearate | 1.61 |

Film Coating: 2-3%

Procedure:
1. Sift all ingredients through suitable sieve.
2. Blend and mix together Lacosamide and Microcrystalline cellulose in a suitable blender and load in Rapid Mixer Granulator.
3. Dissolve and prepare a clear solution of Polyvinylpyrrolidone in solvent.
4. Granulate the Step 2 with the solution from step 3 and dry the granules in Dryer and mill/size them by passing through suitable mesh.
5. Mix and blend the step 4 with Sodium alginate, Hypromellose to form a uniform blend.
6. Mix the blend of Step 5 with Colloidal silicon dioxide and lubricate with Magnesium Stearate for 5 minutes.
7. Compress the step 6 into tablet using suitable punch tooling.
8. Coat the tablets with coating solution either organic or aqueous or semiaqueous solution.

Example 08

| Sr. No. | Ingredients | % w/w |
|---|---|---|
| | Drug loading | |
| | Spray solution/dispersion | |
| 1 | Lacosamide | 13.33 |
| 2 | Hypromellose | 6.66 |
| 3 | Ethyl cellulose | 26.66 |
| 4 | solvent | Q.S. |
| 5 | Sugar Spheres/Microcrystalline Cellulose Spheres | 53.33 |
| | Capsule fill Weight | 100 |

Fill the drug loaded pellets in suitable size of capsule

Procedure:
1. Sift all ingredients through suitable sieve.
2. Dissolve and make a clear solution of Lacosamide, Hypromellose and Ethyl cellulose in solvent under stirring.
3. Load Sugar/Microcrystalline Cellulose Spheres in Fluidized Bed Processor and spray the solution from step 2.
4. Fill the capsule with drug-loaded pellets from step 3.

Example 09

| Sr. No. | Ingredients | % w/w |
|---|---|---|
| | Drug loading | |
| | Spray solution/dispersion | |
| 1 | Lacosamide | 15.62 |
| 2 | Hypromellose | 15.62 |
| 3 | Solvent | Q.S. |
| | Extragranular | |
| 4 | Sugar Spheres/Microcrystalline Cellulose Spheres | 62.5 |

Modified release coating with Eudragit
Fill the drug loaded pellets in suitable size of capsule Procedure:
1. Sift all ingredients through suitable sieve.
2. Dissolve and make a clear solution of Lacosamide and Hypromellose in solvent under stirring.
3. Load Sugar/Microcrystalline Cellulose Spheres in Fluidized Bed Processor and spray the solution from step 2.
4. Dissolve Eudragit RL, Eudragit RS in solvent and add Dibutyl Sebacate.

5. Fill the above drug loaded pellets in suitable size of capsule.

Example 10

| Sr. No. | Ingredients | % w/w |
|---|---|---|
| 1 | Lacosamide | 7.194 |
| 2 | Microcrystalline cellulose | 32.374 |
| 4 | Hypromellose | 32.373 |
| 5 | Polyvinylpyrrolidone/Co-Povidone | 3.597 |
| 6 | Solvent | Q.S. |
| 7 | Crospovidone | 14.388 |
| 8 | Microcrystalline cellulose | 7.194 |
| 9 | Colloidal silicon dioxide | 1.438 |
| 10 | Magnesium Stearate | 1.438 |

Modified release coating coating with Eudragit: 3-4%

Procedure:
1. Sift all ingredients through suitable sieve
2. Blend and mix together Lacosamide, Microcrystalline cellulose and Hypromellose in a suitable blender and load in Rapid Mixer Granulator.
3. Dissolve and prepare a clear solution of Polyvinylpyrrolidone in solvent.
4. Granulate the Step 2 with the solution from step 3 and dry the granules in Dryer and mill/size them by passing through suitable mesh.
5. Mix and blend the step 4 with Co-Povidone, Hypromellose and Microcrystalline cellulose to form a uniform blend.
6. Mix Step 5 with Colloidal silicon dioxide and lubricate with Magnesium Stearate for 5 minutes.
7. Compress the step 6 into tablet using suitable punch tooling.
8. Coat the tablets with above modified release coating solution prepared by dissolving Amino-methacrylate co-polymer type A and type B, Dibutyl sebacate/Triethyl citrate/Polyethylene glycol in an above mentioned solvent.

Example 11

| Sr. No. | Ingredients | % w/w |
|---|---|---|
| 1 | Lacosamide | 7.19 |
| 2 | Microcrystalline cellulose | 32.37 |
| 3 | Hypromellose | 32.37 |
| 4 | Polyvinylpyrrolidone/Co-Povidone | 3.597 |
| 5 | Solvent | Q.S. |
| 6 | Crospovidone | 14.38 |
| 7 | Microcrystalline cellulose | 7.194 |
| 8 | Colloidal silicon dioxide | 1.438 |
| 9 | Magnesium Stearate | 1.438 |

Modified release coating with Eudragit: 7-8%

Procedure:
1. Sift all ingredients through suitable sieve.
2. Blend and mix together Lacosamide and Microcrystalline cellulose in a suitable blender and load in Rapid Mixer Granulator.
3. Dissolve and prepare a clear solution of Polyvinylpyrrolidone in solvent.
4. Granulate the Step 2 with the solution from step 3 and dry the granules in Dryer and mill/size them by passing through suitable mesh.
5. Mix and blend the step 4 with Co-Povidone, Hypromellose and Microcrystalline cellulose to form a uniform blend.
6. Mix Step 5 with Colloidal silicon dioxide and lubricate with Magnesium Stearate for 5 minutes.
7. Compress the step 6 into tablet using suitable punch tooling.
8. Coat the tablets with modified release coating dispersion prepared by Methacrylic acid co-polymer dispersion, Triethyl citrate, Talc and water.

Example 12

Dissolution Study for Lacosamide Tablets of Example 03:

The dissolution profile of the 200 mg lacosamide tablets of Example 03 was carried out in type 1 dissolution apparatus, basket, at 100 rpm, at a temperature of about 37° C., in 900 ml of 0.1N HCl and may release not more than about 25% of lacosamide within 1 hour, from about 30% to about 70% of lacosamide is released within 4 hour and not less than about 75% of lacosamide is released within 12 hours. The results of the in vitro dissolution profile are set forth in Table: 01 and illustrated in FIG. 01

TABLE 01

Dissolution profile of lacosamide 200 mg modified release tablets of Example 03

| Time (Hrs) | Avg. % Drug Release |
|---|---|
| 0 | 0 |
| 1 | 15 |
| 2 | 21.9 |
| 4 | 38.5 |
| 6 | 46.7 |
| 8 | 59.2 |
| 10 | 66.5 |
| 12 | 72.9 |
| 14 | 81.1 |
| 16 | 88.3 |

Example 13

Clinical Study for Lacosamide Tablets of Example 03:

A single dose study was conducted in healthy human volunteers to assess bioavailability of lacosamide formulated as the 200 mg QD modified release tablets of Examples 3 by comparison with a reference treatment with Vimpat® 100 mg tablet BID (each tablet containing lacosamide 100 mg—one tablet each 12 hourly) manufactured for UCB, GA, administered under fed conditions in healthy, adult, male, human subjects in a randomized cross over study and to evaluate safety and tolerability of lacosamide when its absorption profile is altered as in these modified release tablets.

The study design was open label, balanced, randomized, three treatment, three sequence, three-period, single dose crossover bioequivalence study in 12 healthy, adult, male, human subjects under fed conditions.

The pharmacokinetic parameters $AUC_{0-72}$, $AUC_{0-\infty}$, $C_{max}$, and $T_{max}$ were estimated during the study.

Figure 2:
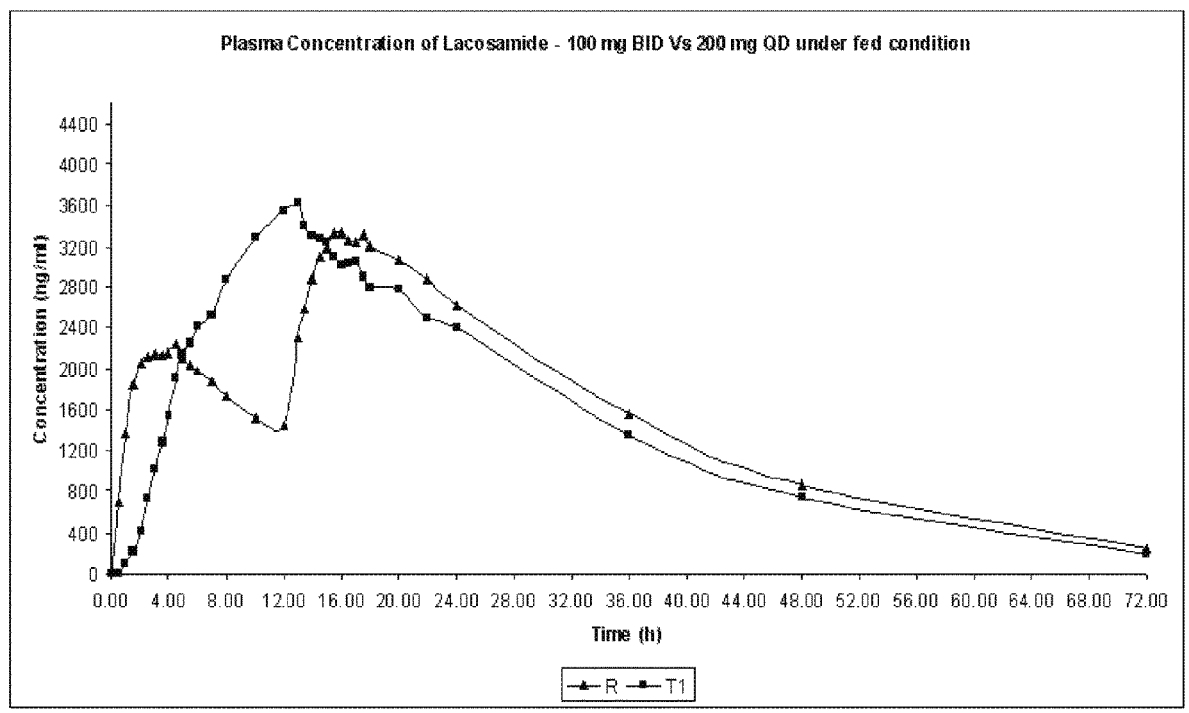
FIG. 02 is a graph depicts the mean plasma concentration-time profiles of lacosamide following a single dose of the formulation (QD) in Example 3 versus 100 mg of the commercially available immediate release tablet (VIMPAT®).

Geometric mean plasma lacosamide concentrations over the 72-hour assessment period are shown in FIG. 02. The pharmacokinetic parameters calculated from mean plasma lacosamide concentration-time profile are given in Table: 02.

TABLE 02

Pharmacokinetic parameters (mean ± standard deviation)

| Parameter | Test (Lacosamide 200 mg modified release tablet (QD)- Example 3) | Reference (Vimpat ® 100 mg tablet(BID) | T/R (%) |
|---|---|---|---|
| $AUC_{0-72}$ (ng · h/ml) | 100606.90 ± 21882.72 | 102700.93 ± 25661.12 | 97.96 |
| $AUC_{0-\infty}$ (ng · h/ml) | 109263.99 ± 24438.17 | 113722.90 ± 27763.30 | 96.08 |
| $C_{max}$ (ng/ml) | 3799.61 ± 733.15 | 3631.46 ± 380.59 | 104.63 |
| $T_{max}$ (h) | 12.00 | 4.50 | — |

The relative bioavailability of the Example 3 formulation to Vimpat® was 97.96% in terms of $AUC_{0-72}$ ratio.

The mean plasma lacosamide concentration profile shown in FIG. 02 clearly shows the tablets of Example 3 effectively modified the release of lacosamide relative to the immediate release tablet (Vimpat®)

The invention claimed is:

1. A once daily pharmaceutical formulation consisting of lacosamide, at least two modified release polymers, and at least one pharmaceutically acceptable excipient, wherein lacosamide is present in an amount of 50 mg to 800 mg in the formulation, and the at least two modifying polymers are present in an amount of about 12% to about 52% relative to the total weight of the formulation and are selected from the group consisting of hydroxypropyl methylcellulose, polyethylene oxide, polyvinylpyrrolidone, ethyl cellulose, copolymers of vinyl pyrrolidone, an alginic acid derivative, hydrogenated vegetable oil and a combination thereof, wherein the pharmaceutical formulation releases in a human subject lacosamide over a period of at least 12 hours from administration to the human subject, and wherein the pharmaceutical formulation is in tablet or capsule form.

2. The once daily pharmaceutical formulation of claim 1, wherein the pharmaceutical formulation contains about 100 mg to about 600 mg of lacosamide.

3. The once daily pharmaceutical formulation of claim 2, wherein the lacosamide is present in an amount of 200 mg in the formulation.

4. The once daily pharmaceutical formulation of claim 2, wherein the pharmaceutical formulation exhibits after administration to the human subject an in vivo plasma profile in the human subject selected from:
   (i) Mean $T_{max}$ of about 5 or more hours, or
   (ii) Mean $C_{max}$ of less than about 4600 ng/ml, or
   (iii) Mean $AUC_{0-72}$ of more than about 78500 ng·hr/ml, or
   (iv) $T_{max}$ at about 12 hours.

5. The once daily pharmaceutical formulation of claim 1, wherein the pharmaceutical formulation releases:
   (i) not more than about 25% of lacosamide within 1 hour, and
   (ii) from about 30% to about 70% of lacosamide within 4 hours, and
   (iii) not less than about 75% of lacosamide within 12 hours
when the release is measured in USP type 1 dissolution apparatus at 100 rpm and 37° C. in 900 mL of 0.1 N HCl.

6. The once daily pharmaceutical formulation of claim 1, wherein the hydroxypropyl methylcellulose is present in an amount of about 6% to about 29% relative to the total weight of the formulation.

7. The once daily pharmaceutical formulation of claim 1, wherein the copolymers of vinyl pyrrolidone is present in an amount of about 24% relative to the total weight of the formulation.

8. The once daily pharmaceutical formulation of claim 1, wherein the alginic acid derivative is present in an amount of about 24% relative to the total weight of the formulation.

9. The once daily pharmaceutical formulation of claim 1, wherein ethyl cellulose is present in an amount of about 27% relative to the total weight of the formulation.

10. The once daily pharmaceutical formulation of claim 1, wherein the hydrogenated vegetable oil is present in an amount of about 8% relative to the total weight of the formulation.

11. The once daily pharmaceutical formulation of claim 1, wherein the pharmaceutical formulation comprises a core comprising lacosamide and a modified release coating.

12. The once daily pharmaceutical formulation of claim 11, wherein the pharmaceutical formulation comprises:
   (i) a core comprising non-pareil seed;
   (ii) a coating disposed on the non-pareil seed with lacosamide; and
   (iii) a modified release coating.

13. The once daily pharmaceutical formulation of claim 1, wherein the at least one pharmaceutically acceptable excipient is a diluent, a lubricant, a glidant, or a combination thereof.

14. The once daily pharmaceutical formulation of claim 1, wherein the at least one pharmaceutically acceptable excipient is a diluent, wherein the diluent is present in the amount of about 6% to about 34% relative to the total weight of the formulation.

15. The once daily pharmaceutical formulation of claim 14, wherein the diluent is microcrystalline cellulose.

16. The once daily pharmaceutical formulation of claim 15, wherein the microcrystalline cellulose is present in an amount of about 7% to about 34% relative to the total weight of the formulation.

17. The once daily pharmaceutical formulation of claim 1, wherein the at least one pharmaceutically acceptable excipient is a lubricant.

18. The once daily pharmaceutical formulation of claim 17, wherein the lubricant is magnesium stearate.

19. The once daily pharmaceutical formulation of claim 1, wherein the at least one pharmaceutically acceptable excipient is a glidant.

20. The once daily pharmaceutical formulation of claim 19, wherein the glidant is colloidal silicon dioxide.

21. A once daily pharmaceutical formulation comprising a capsule shell and a fill, wherein the fill comprises a plurality of granules, wherein each granule comprises a core comprising a non-pareil seed and a coating disposed on the non-pareil seed, wherein the coating consists of lacosamide, at least two modifying polymers, and at least one pharmaceutically acceptable excipient, wherein the at least two modifying polymers are present in an amount of about 34% relative to the total weight of the formulation and are selected from the group consisting of hydroxypropyl methylcellulose, polyethylene oxide, polyvinylpyrrolidone, ethyl cellulose, copolymers of vinyl pyrrolidone, an alginic acid derivative, hydrogenated vegetable oil and a combination thereof, wherein lacosamide is present in an amount of 50 mg to 800 mg in the formulation, and wherein the pharmaceutical formulation releases in a human subject lacosamide over a period of at least 12 hours from administration to the human subject.

22. The once daily pharmaceutical formulation of claim 21, wherein the non-pareil seed is a spherical granule comprising a sugar, microcrystalline cellulose or a combination thereof.

23. The once daily pharmaceutical formulation of claim 21, wherein the at least two modifying polymers are hydroxypropyl methylcellulose and ethyl cellulose.

24. The once daily pharmaceutical formulation of claim 23, wherein the hydroxypropyl methylcellulose is present in an amount of about 7% relative to the total weight of the formulation and the ethyl cellulose is present in an amount of about 27% relative to the total weight of the formulation.

* * * * *